(12) United States Patent
Orband

(10) Patent No.: US 9,217,687 B2
(45) Date of Patent: Dec. 22, 2015

(54) IMAGE ANALYSIS SYSTEM AND METHODS FOR IR OPTICS

(75) Inventor: Daniel Orband, Boxford, MA (US)

(73) Assignee: OPTIKOS CORPORATION, Wakefield, MA (US)

(*) Notice: Subject to any disclaimer, the term of this patent is extended or adjusted under 35 U.S.C. 154(b) by 808 days.

(21) Appl. No.: 13/436,861

(22) Filed: Mar. 31, 2012

(65) Prior Publication Data

US 2013/0258313 A1 Oct. 3, 2013

(51) Int. Cl.
  *G01N 21/35* (2014.01)
  *G01M 11/02* (2006.01)

(52) U.S. Cl.
  CPC ...... *G01M 11/0207* (2013.01); *G01M 11/0292* (2013.01); *G01N 21/35* (2013.01)

(58) Field of Classification Search
  CPC .......................... G01N 21/35; G01M 11/0292
  USPC ....................... 250/338.1; 356/125
  See application file for complete search history.

(56) References Cited

U.S. PATENT DOCUMENTS

| | | | |
|---|---|---|---|
| 3,870,415 A | 3/1975 | Cornsweet | |
| 3,930,732 A * | 1/1976 | Holly | 356/124.5 |
| 4,077,721 A | 3/1978 | Mohan | |
| 4,087,690 A * | 5/1978 | Prober | 250/343 |
| 4,487,502 A * | 12/1984 | Fantozzi et al. | 356/125 |
| 4,767,215 A | 8/1988 | Borodovsky | |
| 4,873,653 A | 10/1989 | Grosskopf | |
| 5,066,120 A | 11/1991 | Bertrand | |
| 5,075,883 A | 12/1991 | Friedman et al. | |
| 5,661,816 A * | 8/1997 | Fantone et al. | 382/100 |
| 2002/0105579 A1* | 8/2002 | Levine et al. | 348/187 |
| 2003/0142302 A1* | 7/2003 | Jiang | 356/301 |
| 2005/0244975 A1* | 11/2005 | Rakow et al. | 436/85 |

FOREIGN PATENT DOCUMENTS

GB 1598648 9/1981

* cited by examiner

*Primary Examiner* — Casey Bryant
*Assistant Examiner* — Jeremy S Valentiner
(74) *Attorney, Agent, or Firm* — Francis J. Caufield

(57) ABSTRACT

A system for quickly measuring and displaying in real-time a variety of performance characteristics of IR optical components such as lenses, or the like. The system is video based and is under the control of a computer which uses a windowing software program to provide the user with a graphical user interface by which the various components of the system and test lenses may be characterized and operated on through functions available via the interface. The system has features for compensating for the presence of IR background radiation that may be present during a measurement cycle and for drift in the video imager. Thermal management features are included to minimize IR background.

23 Claims, 8 Drawing Sheets

IMAGE ANALYSIS SYSTEM AND METHODS FOR IR OPTICS

BACKGROUND OF THE INVENTION

1. Field of the Invention

This invention, in general, relates to optics measurement devices and, in particular, to a real-time optic testing system for quickly performing two-dimensional image analyses on an IR test lens or the like, including the determination of its modulation transfer functions (MTFs).

2. Background of the Prior Art

Today's new technologies for designing and producing complex, high quality IR optical systems require optic measurement equipment that is sophisticated, flexible and accurate.

Often this is achieved by measuring the modulation transfer function (MTF) of an optic, a measure of the ability of an optical system to transfer various levels of detail from object to image. Performance here is measured in terms of contrast (degrees of gray), or of modulation, produced for a perfect source of that detail level. MTF is like other transfer functions used in metrology where a response (output) is related to an input. Examples of systems that can be characterized by a response function are audio equipment, mechanical vibration isolation structures, and seismometers. The Optical Transfer Function (OTF) describes the response of optical systems to known input, and consists of two components—the MTF is the magnitude of the OTF and the phase transfer function (PTF) is the phase component.

The amount of detail in an image is given by the resolution of the optical system, and is customarily specified in line pairs per millimeter (lp/mm). A line pair is one cycle of a light bar and dark bar of equal width and has a contrast of unity. Contrast is defined as:

$$\text{Contrast} = \frac{\text{Im } ax - \text{Im } in}{\text{Im } ax + \text{Im } in}$$

where Im ax is the maximum intensity produced by an image (white) and Im in is the minimum intensity (black). MTF is a plot of contrast, measured in percent, against spatial frequency measured in lp/mm. This graph is customarily normalized to a value of 1 at zero spatial frequency (all white or black). An eye test is a common MTF measurement where an ophthalmologist determines the response of the human visual system (lens and retina) to varying levels of detail-rows of letters. In this way, a doctor determines the frequency response of a patient's visual system.

The Phase Transfer Function (PTF) is a measure of the relative phase in the image as a function of frequency. A relative phase change of 180°, for example, indicates that black and white in the image are reversed. This phenomenon occurs when the OTF becomes negative. Phase reversed images still show contrast and may have a substantial MTF.

MTF specifications are frequently used for optical designs that require repeatable test standards. Some examples are reconnaissance lenses, photographic objectives and IR systems. The MTF measurement instrument is also commonly used as a production quality control tool, since operators are not required to have a high level of optical training in order to properly test the optics.

The benefits of using MTF as a system specification are three-fold. First, in many cases, optical systems employing numerous stages (lenses, film, eye, etc.) have a system MTF equal to the product of the MTF of the individual stage. This can be described as concatenation or cascading of MTF, and allows testing at a subassembly level.

Second, MTF can be specified either at a single wavelength or over a range of wavelengths, depending upon the application. Interferometric wavefront metrology is limited to certain laser wavelengths. MTF allows full spectrum specification and testing.

The third benefit of MTF testing is that it is objective and universal. A test engineer is not required to make judgments of contrast, resolution or image quality. Therefore, under the same conditions, the polychromatic MTF of a lens can be directly compared to the polychromatic MTF of a design, or to another measurement instrument.

There are several methods for measuring MTF—discrete or continuous frequency generation, image scanning, and wavefront analysis. Recent advancements in precision mechanics and electro-optics technologies have produced many practical variations on these methods that allow efficient measurement of OTF to very high accuracy. Four major categories of instrumentation exist: frequency generation, scanning, video and interferometric methods.

The most direct test of MTF is to use an object that consists of a pattern having a single spatial frequency, imaged by a lens under test. An operator measures the contrast of the image directly. This is a discrete or single-frequency measurement. Discrete frequency measurement methods are commonplace. Examples are bar charts, the USAF 1951 resolution targets, and eye charts. A series of such tests can be used to create a graph of MTF over a range of spatial frequencies.

Various mechanisms have been developed for continuously varying the source frequencies while constantly measuring the image contrast. One example of this approach utilizes a rotating radial grating with a slit aperture as an object. A pinhole is placed in the focal plane of the lens and the light passing through it is monitored with a detector. As the grating rotates, the individual black and white bars are swept across the pinhole. By moving the grating relative to the slit, the spatial frequencies of the object can be varied. The detector output is synchronized to the rotation and is a direct measure of the MTF at the radial grating spatial frequency and its harmonics.

The obvious advantage of frequency generation methods is the fact that the output is directly measured. The major disadvantage is that these methods require the simultaneous manipulation of sources and detectors, which limits instrument flexibility.

Most commercially available MTF measurement instruments use a form of image scanning. Scanning systems operate on the principles of linear system theory—the image produced by the lens with a known input, such as an infinitesimally small pinhole, is determined and the MTF is computed from this information.

Measuring MTF with this method is the optical analogy of measuring the frequency response of an audio speaker. The image produced by a lens of an infinitely small source of light will be a blur, much as the output of a speaker with a single input audio frequency will be tonal. The qualities of the blur similarly indicate the frequency response of the lens. The spatial profile of the image is called the line spread function (LSF) if the scanning is one-dimensional, or the point spread function (PSF) for two-dimensional scanning. An LSF is commonly produced by edge-scanning an image of a point source with a mechanical obscuration (knife-edge) while monitoring the intensity throughput, and then differentiating the output. It can also be produced by using a slit source and moving a pinhole or slit. The vertical or horizontal orientation of the knife determines whether sagittal or tangential scanning is achieved. If the knife-edge possesses a right angle and is diagonally traversed across the image, it will sequentially scan in the horizontal and vertical directions, yielding both sagittal and tangential edge traces. The Fourier transform of the LSF is the one-dimensional MTF.

For a true impulse response function to be derived, the finite source size must be corrected. Through linear system theory, it can be shown that this correction consists of dividing the measured MTF by the Fourier transform of the source, such that the corrected MTF data is the quotient of the uncorrected MTF data divided by the proper correction factor at discrete frequencies.

Computer algorithms quickly correct measured MTF data for finite aperture sizes (slits, pinholes, etc.). The fully corrected data can then be compared to the theoretical performance.

Through-focus MTF mapping can be generated by remeasuring the MTF at different focus planes. The effects of spherical aberration, defocus, astigmatism, field curvature and chromatic aberration can be determined from these curves. By choosing a single spatial frequency and comparing the MTF at these focal planes, the focus for best (or balanced) performance can be determined. Very high resolution (without image magnification) can now be achieved with scanning systems equipped with precision lead screws driven by stepper motors or accurate synchronous motors.

A drawback to image scanning methods is the duration of scan. Sampling theory and the parameters of the lens under test dictate the number of data points required for a properly sampled image. Insufficient sampling can significantly affect the accuracy of the MTF. Often, a long image scan will require upwards of 30 seconds measurement time.

Video methods are subject to the same theoretical considerations as the scanning methods. Typically, a solid state array is placed at the focal plane of the lens-under-test. If a pinhole source is used, the point spread function can be directly obtained from the digitized video output. The two-dimensional OTF is obtained by directly Fourier transforming this data in two dimensions. Edge traces and line spread functions can be obtained by integrating the point-spread function. If a slit source is used, the line-spread function is obtained directly and the OTF is calculated by performing a one-dimensional Fourier transform of this. In either case, the MTF is given by the modulus of the OTF. An example of a video system is described in detail in U.S. Pat. No. 5,661,816 issued on Aug. 21, 1997 in the name of Stephen D. Fantone, et al. and entitled IMAGE ANALYSIS SYSTEM.

The advantage of video MTF measurement lies in the speed with which it can be accomplished. The MTF can be updated as quickly as the solid state array can be electronically sampled and the Fourier transform calculated. This provides a continuously updated spread function and MTF curve. Video systems are very useful for alignment of optical systems specified by MTF data. An operator can move an optical component or assembly and monitor the effects of that perturbation on the MTF.

The drawbacks of video methods are inherent in the design of electronic solid state arrays. Since detector element sizes are finite and on the order of many microns, the maximum resolvable frequency is approximately 30-80 lp/mm. This problem can be circumvented by adding an optical relay system to magnify the image onto the array. However, the relay optics must be very high quality, must have a very high numerical aperture to capture the entire output of fast lenses or systems working at high off-axis angles, and should be essentially diffraction limited to not impact the measured MTF.

Pixel to pixel crosstalk, both optical and electrical, tend to increase the apparent image size and affect the measured MTF. The MTF should be corrected for these effects. High-speed video digitizing boards commonly digitize with 8-bit precision. The illumination on the video camera must be controlled so as not to saturate pixels or cause blooming. The accuracy of the computed MTF is limited by the level of digitizing. Eight-bit video MTF systems are less accurate than conventional scanning systems. However, with the right application, video-sampling methods are valuable.

Interferometric Methods

The MTF of a system may be measured with an interferometer by one of two methods: auto-correlating the pupil function of the lens-under-test or analyzing the PSF calculated by Fourier transforming the pupil wavefront. This is very convenient for systems which are suitable for testing in an interferometer and do not exhibit significant chromatic aberrations, and whose wavefront errors do not vary substantially over the wavelength of interest. With scanning, video or discrete frequency methods, the wavelength range can be adjusted by using wide band sources and spectral filters for full polychromatic testing. Interferometers rely on monochromatic sources (i.e. lasers) so that MTF is only available at these wavelengths.

In addition, since phase measuring interferometers have limited wavefront sampling capabilities, the wavefront should be fairly well corrected. Lenses with excessive wavefront errors are difficult to measure with interferometers.

Measuring MTF in the infrared has become nearly as commonplace as measuring MTF in the visible. Most IR measurements involve physical scanning apertures very similar to visible measurement scanners in both the 3-5 µm and 8-12 µm spectral bands. With advent of inexpensive IR video cameras and blackbody sources, video analysis systems are also possible.

However, measurement in the far IR region of the spectrum (FWIR), between about 8-15 micrometers, whether using scanning or video detection, is not without problems. Despite the use of sensitive IR detectors and high temperature black-bodies, the most significant challenge facing IR measurements is the signal/noise ratio. Thermal background emissions coupled with "slow" lenses (those having a large f/#) raise noise and reduce signal levels. The choice of source (slit or pinhole) dimensions is determined by the maximum frequency of interest and the magnification of the lens under test. For example, if the magnification of the optical system is 0.1×, a 200 µm pinhole diameter or slit width will allow band-limited testing to 25 lp/rm. If frequencies beyond this limit are desired, the source area must be decreased, and the signal-to-noise will decrease by a corresponding amount.

To give a sense for the effect that background IR can have on contrast measurements, assume that it is on around 30 percent of the signal. The contrast then is about 0.5 whereas, if the background is only 5 percent, the contrast will be about 0.9. Thus, the presence of background IR in the field of view of the detector is a very serious problem for MTF calculations if not properly managed.

Accordingly, it is a principle object of the present invention to provide an IR image analysis system that minimizes IR background levels with proper thermal management.

It is another object of the present invention to provide methodology and apparatus for compensating for the presence of IR background radiation in an instrument's measurement path so that MTF and other optical properties of IR optics can accurately be determined.

It is another object of the present invention to provide an instrument for measuring the modulation transfer function of IR optics in real-time while providing a convenient display of the results.

It is another object of the present invention to provide an instrument for measuring the performance of IR optical systems by performing real-time, two-dimensional image analysis and displaying the results through the use of computer system with a graphical user interface.

Other objects of the invention will, in part, appear hereinafter and, in part, be obvious. A full understanding of the invention will be had from the detailed description when read in connection with the accompanying drawings.

SUMMARY OF THE INVENTION

A system for quickly measuring and displaying in real-time a variety of performance characteristics of IR optical components such as lenses, or the like. The system is video based and is under the control of a computer that uses a windowing software program to provide the user with a graphical user interface by which the various components of the system and test lenses may be characterized and operated on through functions available via the interface. The system has features for compensating for the presence of IR background radiation that is present during a measurement cycle as well as for drift in the video imager. Thermal management features are included to minimize IR background.

In accordance with one embodiment of the invention, apparatus for testing infrared (IR) optics is provided. The apparatus comprises an arrangement for holding and positioning an IR optic to be evaluated along an optical path of the apparatus so that it can form images when illuminated with IR radiation. A source of radiation emits IR radiation for travel along the optical path over a spectral band that at least encompasses the operating wavelength of the IR optic being tested. An optical system is arranged along the optical path for directing IR radiation from the source for travel toward the IR optic. A mechanism operates to selectively block and unblock the optical path during a predetermined period. The mechanism has a first position in which it blocks IR radiation and at least one other position in which it presents a preselected transmissive target to the IR optic. The temperature of the mechanism remains unchanged from the beginning to the end of the predetermined period so that, while blocked, only background IR radiation reaches the IR optic, and while unblocked, IR radiation from a transmissive target, along with background IR radiation, reaches the IR optic. An IR camera having an image detector is provided for observing the image plane of the IR optic to generate images of the blocked optical path and transmissive target. The intensity of which these images vary as a function of spatial location on the IR image sensor of the IR camera. A processor operates to determine from the images the background IR radiation present in the optical path. Afterwards, the processor adjusts the image data for the by providing corrected image data from which line spread functions are calculated. Subsequent Fourier analysis of the line spread functions are carried out to determine MTFs.

Use is made of bandpass filters, gold reflective coatings, housing thermal masses and housing interfaces with low heat conduction are used in conjunction with heat removal features to assure that blank and transmissive targets are substantially the same temperature during measurement cycles.

In accordance with another embodiment of the invention, a method for testing infrared (IR) optics is provided and comprises holding and positioning an IR optic to be evaluated along an optical path so that it can form images when illuminated with IR radiation. IR radiation from a source is directed for travel along the optical path toward the IR optic. The optical path is selectively blocked and unblocked over a predetermined period with blank and transmissive targets while maintaining the temperature of the blank and transmissive targets substantially unchanged from the beginning to the end of the predetermined period so that, while blocked, only background IR radiation reaches the IR optic, and while unblocked, IR radiation from the transmissive target along with background IR radiation reaches the IR optic. The image plane of the IR optic is observed with an IR camera to generate images of the blank and transmissive targets the intensity of which vary as a function of spatial location on the IR detector of the IR camera. From the blank target, the background IR radiation present in the measurement path is determined. Afterwards, the intensity levels in the image of the transmissive target are adjusted by pixel averaging to compensate for background radiation to generate compensated image data representative of the optical properties of the IR optic. Then; image analysis is performed on the compensated data and the results displayed as the image analysis is performed. During the image analysis line spread functions, Fourier analysis, and MTF calculations are carried out.

BRIEF DESCRIPTION OF THE DRAWINGS

The structure and operation of the invention, together with other objects and advantages thereof, may best be understood by reading the detailed description to follow in connection with the drawings wherein the same reference number is used throughout the drawings to identify particular parts wherever they appear and wherein.

DETAILED DESCRIPTION

The present invention is a video-based metrology system for accurately measuring optical performance characteristics of optical systems designed to operate in the long-wave infrared (LWIR) waveband of the spectrum. As will be seen, the inventive system compensates for the time-varying DC offset introduced by the video sensor it employs and also for unwanted background IR that may be present in its optical measurement path during a measurement cycle. Thermal management features are provided in the system to reduce the presence of unwanted IR background radiation generated by the system itself, reduce the amount of ambient IR that may enter the measurement path open to its surrounding environment, minimize heat transfer at interfaces between its IR source and subassemblies downstream of the source, cool system housings passively, and reflect unwanted IR radiation from propagating from the source to downstream elements involved in measurements.

Figure 1:
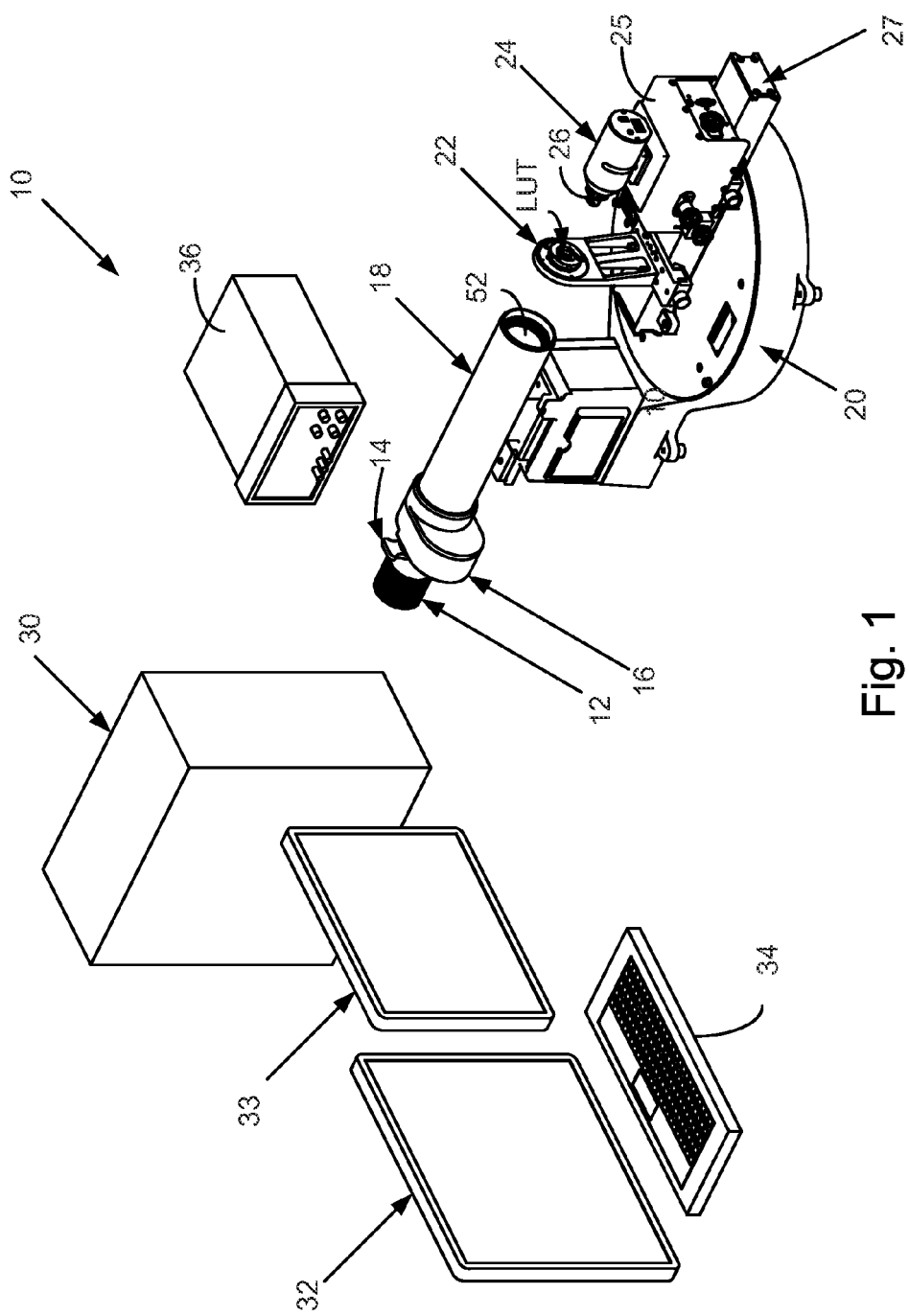
FIG. 1 is a diagrammatic perspective view of the IR metrology system of the invention.
Figure 2:
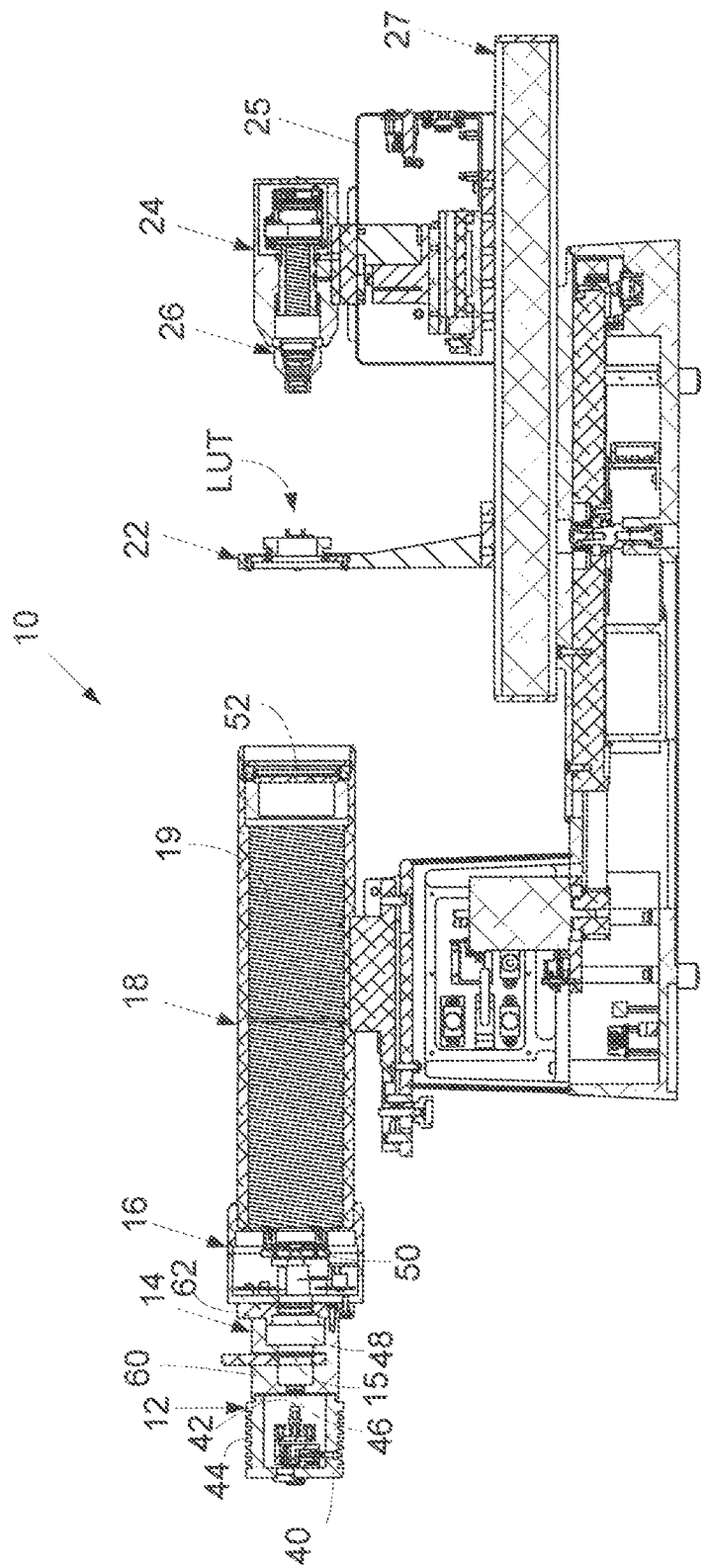
FIG. 2 is a diagrammatic cross-sectional elevational of the metrology system of FIG. 1 absent its computer, keyboard, monitors, and power supply.

Referring now to FIGS. 1 and 2, the inventive LWIR metrology system is shown generally at 10. System 10 comprises, in order from source to imager, an IR source housing 12, a bandpass filter housing 14, a target wheel housing 16, a collimator barrel 18, a rotary stage 20 atop of which sits a holder 22 for lenses, or the like, to be tested (LUT), a low-cost digital IR camera 24 that sits on a truck 25 that is slidable on an optical rail 27, and a relay lens 26. Holder 22 and truck 25 may be positioned for and aft along the optical axis of the system to adjust axial spacing between the end of the collimator barrel, the position of the LUT, and the IR camera 24. IR camera 24 may also be moved side to side with respect to truck 25 to adjust lateral positioning between it and the LUT. Rail 27, and those components mounted atop it, can be rotated with respect to the system optical axis. A power supply or source 36 (e.g., BK Precision 1666) provides electrical power to an IR lamp (shown at 42 in FIG. 4, for example, a Hawkeye Technologies IR-12K) and utilized in system 10. IR camera 24 is preferably a FLIR Tau 320 or equivalent.

System 10 and its operation are under the control of a computer 30 that is equipped in a well-known manner with a computer program that provides a user with a convenient graphical user interface for characterizing the various components of the system itself, identifying test lenses and their performance specifications, and carrying out, displaying, and recording a variety of image analysis operations, including the calculation and display of the two-dimensional MTF. Commands, operations, and data are displayed on a system monitor 32 and an alignment monitor 33. A keyboard 34 serves as an input device in the usual way and a mouse or other pointing device (not shown) are used to indicate and select commands or operations that are displayed on monitors 32 and 33. Computer 30 also carries out various calculations, provides memory for storage, and performs housekeeping functions as needed from time to time.

Figure 3A:
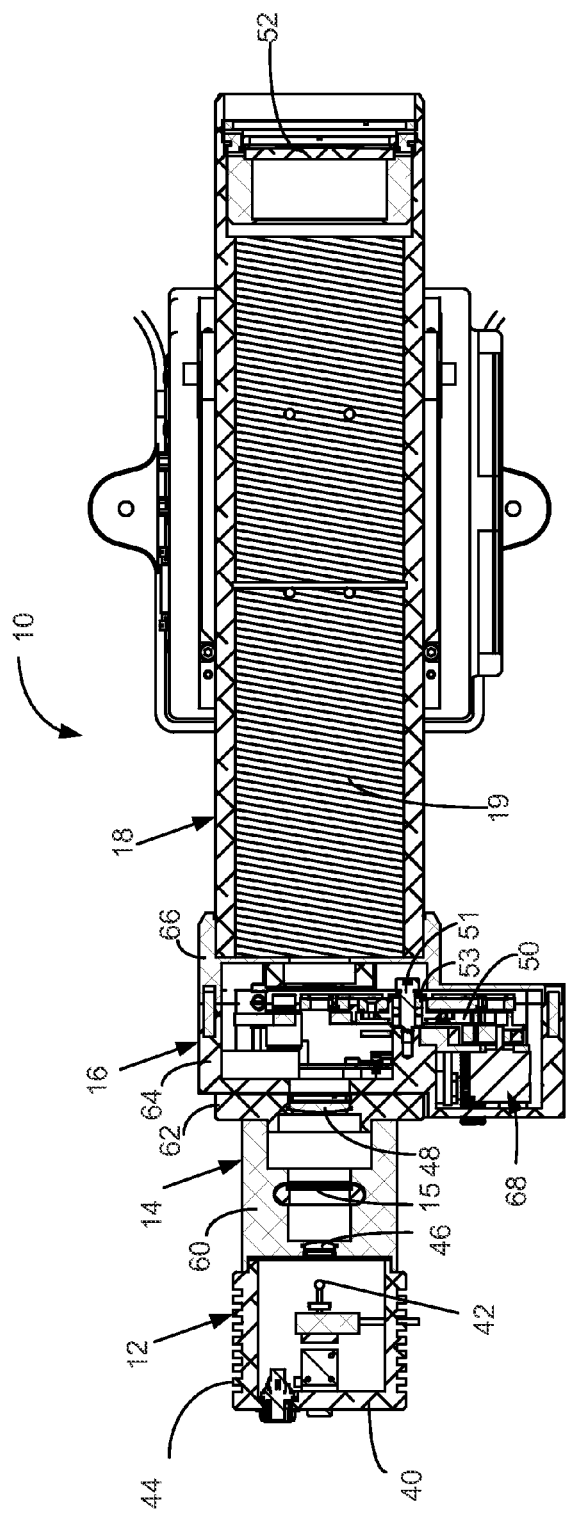
FIG. 3a is a diagrammatic cross-sectional planar view of a portion of the system of FIG. 1 that includes components from its IR source housing to the end of its collimator barrel.
Figure 4:
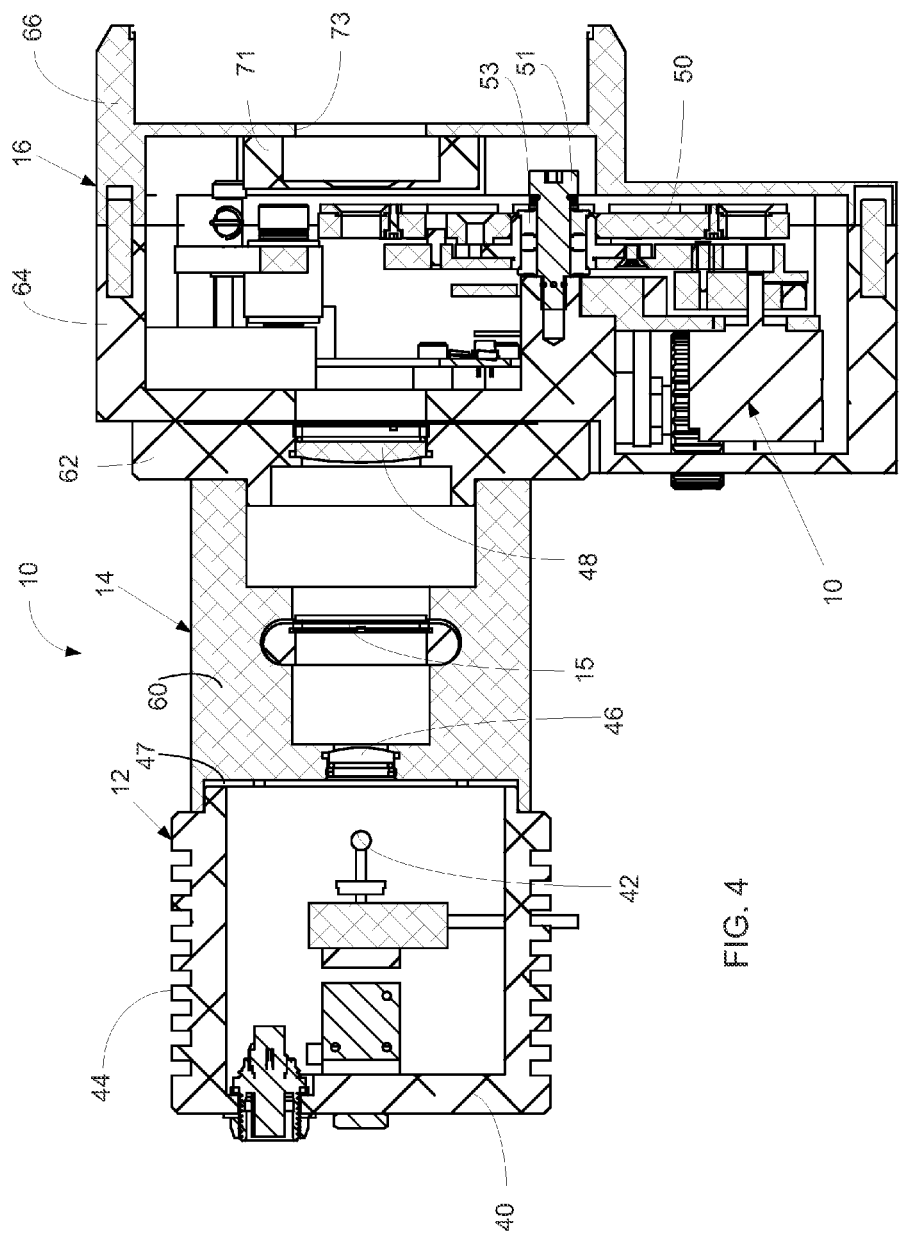
FIG. 4 is an enlarged diagrammatic planar cross-sectional view of the IR source housing, bandpass filter housing, and target wheel housing of the system of FIG. 1.

Referring now to FIGS. 3a and 4, it can be seen that IR source housing 12 comprises a housing 40 made preferably of aluminum. Inside housing 40 there is an IR source 42. IR source 42 is a filament wound wire source operating at 1000° C. and having a color temperature of about 1273° K. The wavelength of radiation emitted by source 42 is in the 8 to 12 micron range. Power supply 36 provides a controlled current to source 42 and is monitored to maintain its output substantially constant. Such sources are available from Hawkeye Technologies as indicated above. It will be evident that source 42 may be operated at other temperatures to alter its spectral output and that other sources may be used in its place to provide emissions at other desired wavelengths.

Housing 40 is provided with cooling fins 44 to dissipate heat built up inside it thus removing heat that could otherwise be transferred to system structure downstream of IR source housing 12.

Source housing 12 is connected to bandpass filter housing 14) via a flanged mechanical coupling arrangement (See FIG. 4) that is structured to have minimal physical contact between the two so as to reduce the possibility for heat transfer from the source housing 12 to forward elements of system 10. In this connection, there is also a small air gap 47 formed between source housing 12 and bandpass filter housing 14 to further reduce the possibility for forward heat transfer. The rearward surface of bandpass filter housing 14 (facing source 2) may also be provided with an IR reflection coating to direct unwanted IR radiation rearwardly where it can be eliminated via cooling fins 44.

Figure 3B:
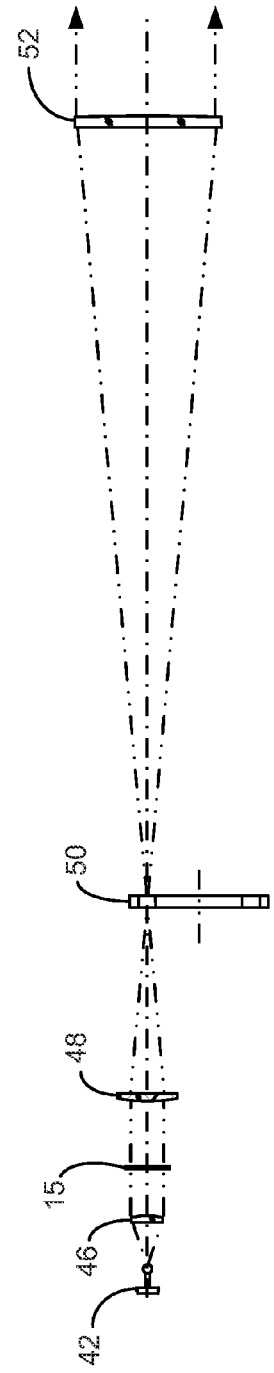
FIG. 3b is a diagrammatic view tracing rays propagating along the optical axis of the system from its IR source and exit the collimating barrel.

An IR bandpass filter 15 resides in housing 14 which has a mechanical coupler 60 to interface with housing 40.and a downstream flange 62. Bandpass filter 15 comprises a multilayer coating structured in a well-known manner to reflect unwanted IR radiation, i.e. radiation outside the operating wavelength of the LUT, while transmitting IR radiation within the wavelength regions at which the LUT is designed to operate and thus tested. To assure that bandpass filter 15 provides uniform transmission and reflection properties across its effective operating area, it is positioned in a collimated beam that is generated by a collimating lens 46 (see also FIG. 3b) that accepts radiation from source 42 and converges it as shown in FIG. 3b. For this purpose collimating lens is preferably of plano-convex form and made of a suitable IR transmitting optical material such as ZnSe or the like. It should be noted that IR radiation retroreflected by bandpass filter 15 back towards source 42 ultimately is absorbed by coupler 60 and housing 12 after which it is dissipated as heat to the ambient air surrounding system 10.

As best seen in FIG. 4 and FIG. 3b, flange 62 is configured to position and support a converging convex-piano lens 48 of IR transmissive material in the path of the collimated beam formed by collimating lens 46. Converging lens 48 focuses this collimated beam to a plane in which various targets reside in a rotatable wheel 50 that carries a series of targets 70 through 92 (See FIGS. 5a and 5b) that are indexed either manually or under computer control between predetermined spaced apart, preferably equal, angular separations so that different targets can be illuminated by radiation focused by converging lens 48.

Target wheel 50 is mounted for rotation in a pair of mated housing halves including a rear housing half 64 on the source side and a front housing half 66 upstream of it. To this end, target wheel 50 is attached to rear housing half 64 via a center bolt 51 that passes through a stainless ball bearing 53. This mounting arrangement minimizes the amount of stray heat that may be transferred to target wheel 50 while still facilitating its rotation. Target wheel 50 is automatically indexable to present different, targets to the LUT by means of well-known motors and gear arrangements designated generally at 68 and operating under the control of computer 30, or alternatively, can be manually rotated between different angular locations using a well-known detent mechanism.

Figure 5:
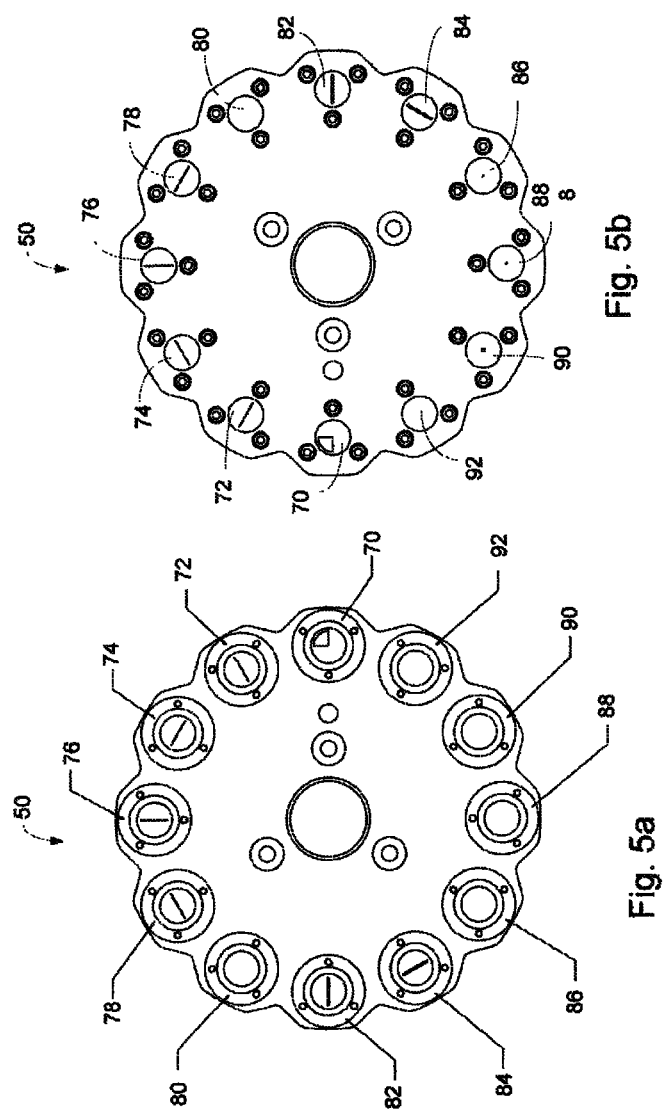
FIGS. 5a and 5b are, respectively, diagrammatic rear and front elevational views of a target wheel used in the system of FIG. 1.

Reference is now made to FIGS. 5a and 5b which diagrammatically show rear and front elevations, respectively, of target wheel 50 where both elevations are perpendicular to the optical axis of system 10. FIG. 5a shows the rear side of target wheel 50 as it faces source 42 while FIG. 5b shows target wheel 50 as it faces the LUT. As seen, target wheel 50 carries 11 targets (70-90) and one blank 92 all of which are spaced 30 degrees apart. The targets per se comprise pinholes of different diameters, slots of different width, length, and orientation, and one 90-degree pie segment 70. As will be seen, the targets are imaged by LUT to an image plane and afterwards relayed or magnified as needed to finally be imaged onto the IR sensor of camera 24. In this connection, there is an appropriate pinhole diameter or slot width for particular LUTs. Slot width is given by:

$$1 \Big/ \left( \frac{1}{\lambda} f\#4 \frac{TestEFL}{CollimatorEFL} \right)$$

where f# is the numerical aperture of the LUT; EFL is the effective focal length of the LUT or collimator lens, and λ is typically is 10μ or the higher end of the range for operating wavelengths of the LUT.

The surfaces of back side of targets 70 through 92 are coated with gold to retroreflect any unwanted IR radiation that may be incident on them. Thus, IR radiation outside of the operating range of the LUT striking the rear side of a target is reflected back toward source 42. The front side of the targets are painted with a flat black paint such as Mankiewicz Nextel Suede Coating 3101 to reduce the effects of any unwanted radiation striking the front side of a target. In conjunction with the previously discussed thermal management features, the relative thermal masses of the various housings of system 10, and the thermally isolating mounting of the target wheel 50, the gold coatings operate to maintain the temperature of each of the targets substantially uniform so that all of the target emit virtually the same IR radiation especially when considered over a small time period as will be explained more fully below.

Referring again to FIGS. 3a and 4, it can be seen that front housing 66 includes a baffle 71 that surrounds an aperture 73 sized to limit the diameter of the bundle of rays that are emitted into the collimator barrel 18 that is provided with a singlet collimating lens 52 of convex-plano form and fabricated of IR transmissive material. The size of aperture 73 is such that the bundle of rays reaching collimating lens 52 is slightly larger than needed to assure that its entrance pupil of lens 52 completely filled.

The interior of collimating barrel 18 is provided with threaded baffling 19 to reduce the effects of any unwanted radiation that may enter it from the ambient surrounds via collimating lens 52. Baffle 71 further operates to reduce stray radiation from reaching the front side of a target.

FIG. 3b shows the path that rays travel in propagating through the optical components system 10 from source 42 to collimating lens 52. By design, the filament of source 42 is imaged onto a selected target positioned in alignment with the optical axis of system 10 by target wheel 50 while the pupil of lens 46 is imaged onto the pupil of collimating lens 52. As seen, a collimated beam exists between lenses 46 and 48 where bandpass filter 15 resides, and a second collimated beam is formed by collimating lens 52 to travel along the optical axis where it is incident on an LUT. The LUT, in turn, images a selected target to an image plane after which it is imaged by IR camera onto its internal 2D IR image sensor via a relay lens 26. Magnification may be introduced as needed to assure that the size of the image on the image sensor is of suitable scale to cover an optimal number of pixels and thus maximize the amount of data points available for calculating the optical performance characteristics of the LUT. By observing the image plane of the IR LUT with IR camera 24 images of blank and transmissive targets are generated whose intensity varies in a well-known manner as a function of the spatial location on the IR image sensor of IR camera 24. That is, a digital image signal is generated with outputs corresponding to image pixel intensity in correspondence with pixel location. Relay lens 26 has a numerical aperture large enough to capture the light exiting the IR optic under test and is diffraction limited for accurate line spread function and MTF measurements.

MTF of the targets themselves is known and each target is constructed in a well-known manner such that its spatial frequency content encompasses that expected of the LUT and its intensity level or modulation are sufficient to generate appreciable signal levels when corrected in a manner to be described. As mentioned above, a target may be a slit for one-dimensional analysis or pinhole for two-dimensional analysis, or any other well-behaved target with analytically predictable properties. In addition, a target may be at infinite or finite conjugates. In either case, its characteristics are definable in well-known terms that are inputted into the system program for purposes of performing the various image analysis operations to be subsequently described. In the case of two-dimensional MTF determinations, the target is preferably a pinhole which is imaged more or less perfectly by the LUT at some focal or measurement plane behind it. As indicated above, this image, in turn, is re-imaged by objective 26 onto the IR image sensor of digital IR camera 24. The image has an intensity distribution from which the line spread function of the test lens can be derived along at least one azimuth. The camera image sensor is preferably two-dimensional with sufficient pixel elements of a scale with a corresponding spatial frequency able to resolve to analyze the LUT image.

The size of the image of the blur circle formed by lens 26 on the camera image sensor can be made larger or smaller in accordance with the magnification of lens 26. Thus, for a low magnification or a magnification of unity, the image preferably covers an area of, say, about 2×2 pixels square to provide the system with one first effective apparent spatial resolution. If the apparent resolution of the image sensor needs to be higher, it can be increased by increasing the magnification of lens 26 to provide a larger image of a target on the image sensor. In other words, the effective spatial resolution of the image sensor can, as required, be increased simply by changing the magnification of the image formed by LUT, and this information is provided to the program as part of its setup or configuration so that it will know what the testing conditions are for purposes of performing the image analysis calculations it carries out. What is essential here is that the pixel geometry is known.

Figure 6:
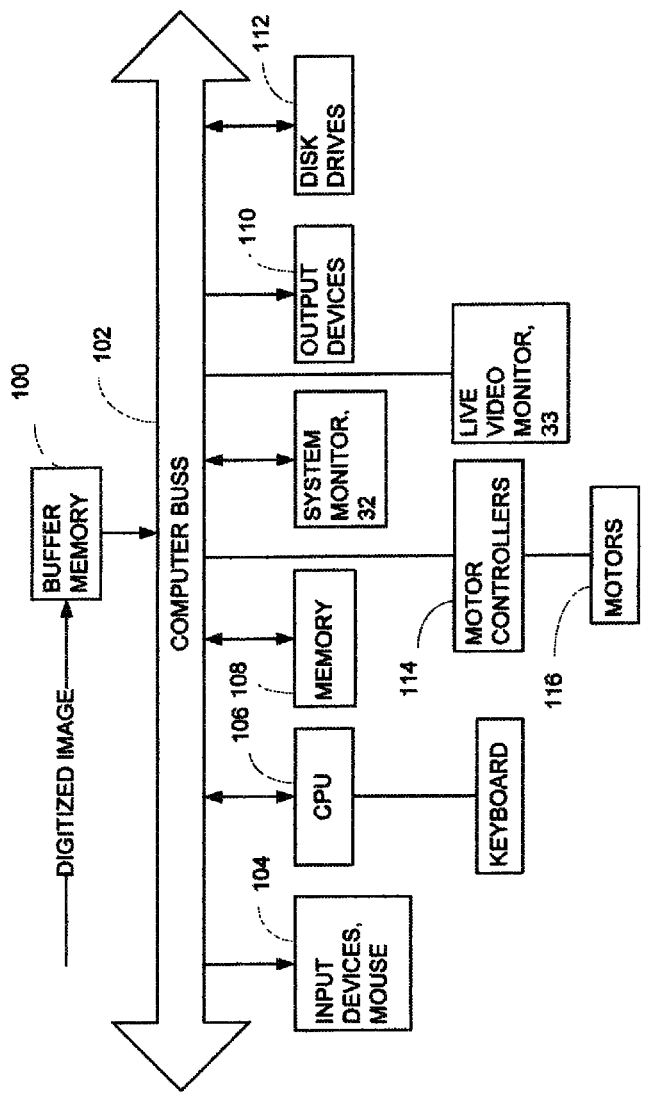
FIG. 6 is a schematic block diagram of various system components from FIG. 1 for performing image analysis and displaying, controlling, and operating the system.

As mentioned, the output of camera 24 is in the form of a standard digital video signal as shown in FIG. 6. This output, which represents the intensity distribution in the image formed by LUT, is fed into and then stored in a buffer memory 100. The digitized image is formed at the repetition rate of the camera image sensor so that the contents of buffer memory 100 are repeatedly updated until such time as a command is received via the GUI manner to freeze the contents of buffer memory 100 and transfer them to computer 30 via its bus 102.

Bus 102 also has connected to it a computer CPU 106, memory 108 in the form of hard drives, RAM, and ROM, system monitor 32, disk drives 112, input devices including mouse 104, motor board 116 connected via a well-known motor controller 114, live video monitor 33, and output devices 110 which could be, for example, printers or plotters or the like. All of the devices connected to bus 102 are under the control of a bus interrupt management scheme well-known in the related arts. Keyboard 34 is connected directly to CPU 106.

Once the digitized video image is transferred to computer 30, it is thereafter operated on by internal program algorithms to analyze, display, print or record the performance of an LUT.

The program for carrying out the functions of system 10 as described below is preferably based on a windowing environment such as those marketed by Microsoft® or Apple®. The preferred implementation is by way of Microsoft® Windows, but it can just as easily have been implemented via any other with similar features.

A user of system 10 has two software operational modes, manual and automatic (macro driven). Data is acquired by choosing either "Real time scanning" or "Through focus scanning". The user visually selects the area of the image of interest with cross hairs, then witnesses the acquisition process. And, then with the push of a mouse button, captures the data into memory. Captured data is then put into a sub or child-window on the main screen, and can then be reviewed, compared to specifications or other pre-existing data, arranged for preferable viewing, and printed. At this point, the windowing features are of full advantage. Any function of the program, including the entire data entry, acquisition, capture, and print processes, can be fully automated by use of the macro language. Therefore, users can set up pre-set routines for the lenses under test and implement these routines as desired. For example, test routines can be set for (1) eyepiece, (2) objective, (3) relay lens, etc., and called up from memory as appropriate. The user can have stored specifications for any number of pre-identified test optics.

The program also has the ability to drive up to four individual motors directly from the code. The motors can be utilized to set focus, adjust spacings, change incident angle, rotate mirrors, etc. The motor movements can be contingent upon retrieved data. For example, the motor may continually focus the lens under test until the MTF exceeds some predetermined level.

The interface and software architecture developments that are characteristic of windowing environments have been advantageously exploited in the implementation of the invention.

The programs functionality has been carefully designed to permit the use of readily available system components from different manufacturers to provide a high degree of flexibility and portability by allowing the user to inform the system what components are being used, how they are configured, and under what conditions they will be used to carry out the required tests.

Traditional computer user interfaces were command line driven, forcing a user to respond and adapt to an application programs' processing sequence (as required by early batch processing models—one program at a time; one line at a time). Essentially, the program, its structure, and its limited methods of giving and receiving input (only capable of processing character data) drove user behavior. Windowing environments are an implementation of Graphical User Interfaces. There are a number of windowing architectures based on various hardware/software and industry standards. Due to their commitment to standards and graphical orientation, they tend to be easier to learn and use and enhance application integration (data sharing). Microsoft® Windows® is one of these implementations.

Most windowing environments share a number of characteristics such as:
A Graphical Extension to the operating system
Standard interface and user interface objects such as Windows, Icons, Menus, and dialog boxes (or buttons) providing a consistent "look and feel" to users regardless of the application. Windows provide a view of data currently in the computer. Icons are small graphical objects which represent either commands or active processes or programs. Menus provide a consistent mechanism for selecting application functions or navigation.
Multi-tasking
Standard Application Programming Interface supporting the user interface and processing model. This provides a programmer with a set tools and a re-usable library of routines (code) to reduce application development time. These routines automatically provide adherence to MS windows standards (ie creation of user-interface objects, managing computer resources, message handling, managing the graphics display, and so on) while still allowing development flexibility and creativity.

Having described the general features of the windowing environment, the specific functions of the particular program for use in carrying out the methods of measurement of the present invention will now be taken up. The supporting software code for providing those features was implemented in the "C" language through the use of Microsoft's Windows Developers Toolkit. For a more detailed description of the type of functionality that can be provided using the windowing environment, reference may be had to U.S. Pat. No. 5,661,816 issued to Stephen D. Fantone, et al. on Aug. 26, 1997, the entire contents of which are incorporated herein by reference. It will be recognized that the functions described in the '816 patent may be identically used herein except that there is in addition a correction procedure for compensating for the presence of image sensor drift and the presence of background IR in the measurement path.

Figure 7:
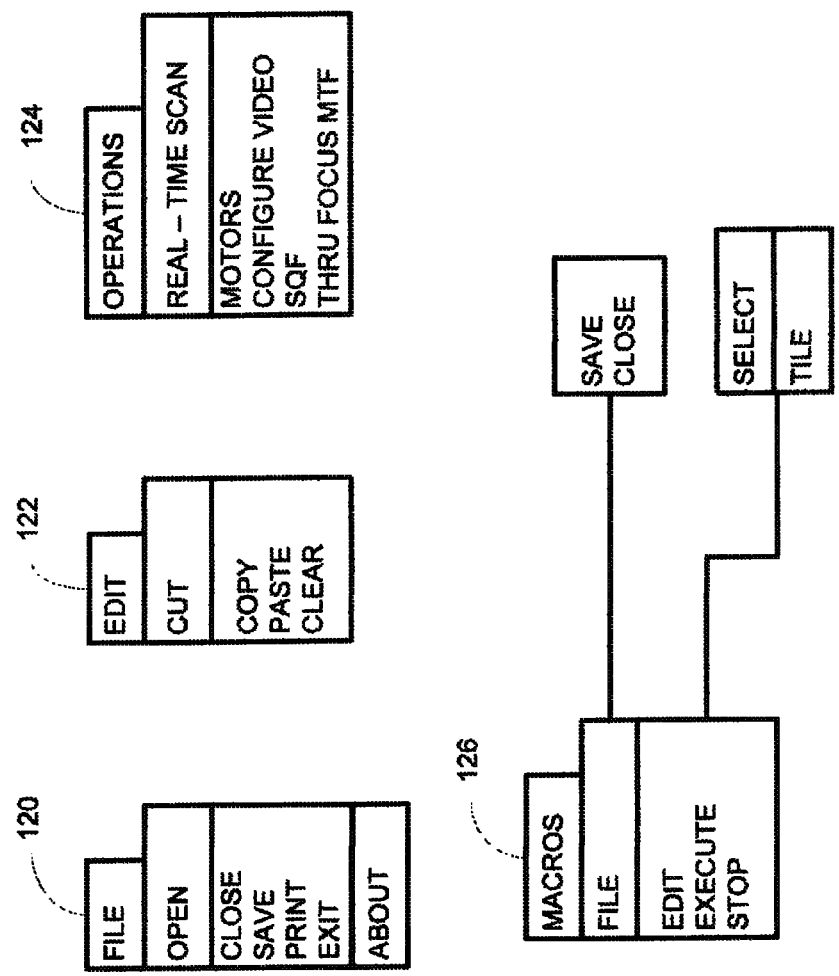
FIG. 7 illustrates the drop-down menus from the "File", "Edit", "Operations" and "Macro" functions available as options under the main window menu bar.

FIG. 7 shows at 120 the general drop-down high level menu structure appearing in response to activating the "File" option from a menu bar and its options have the following functions:
Option Description
"Open" Displays a dialog box in which the user opens a file which may include information describing various system components, lens specification, configurations, data, etc.
"Close Displays a dialog box in which the user closes a file providing it with a name and location.
"Save" Saves a file to a designated directory
"Exit" Exits the program and returns to Windows Main Window or an MS-DOS Executive window.
"Print" Displays a dialog box in which the user the current file or other designated file.
"About" Provides information about file activities.

At 122 is shown the "Edit" drop-down menu where its options have the following function:
Option Description
"Cut" Moves text out of a file and into Clipboard, a temporary storage device that holds text being moved from one file to another.
"Copy" Copies highlighted text into Clipboard.
"Paste" Transfers the contents of Clipboard to another window.
"Clear" Clears the contents of the screen buffer.

The "Macros" option is shown at 126. With it, the user may create, edit, execute, stop, save and close files which include sequences of commands. The commands allow setting of all configuration, data, execution of testing sequences, communication and status checking of input/output ports, and algebraic and mathematical functions. These latter functions allow analysis of measured data, comparison to stored values and conventional algebraic operations. For instance, the macro language can provide for the calculation of the ratio of MTF's measured at different spatial frequencies, or even comparison of the MTF's as measured on two different lenses. The macro language can prompt the user for input and inform the user of the status of the macro execution. The macro language is also of great utility in standardizing a particular set of test sequences and automated testing sequences. In the latter case, the macro language can check the status of an I/O port to see if a lens has been loaded for test. If the indicated status is yes, then the test sequence can be executed and comparison of the results can be made on a go/no-go basis or some other performance criteria made. The results of these tests can then be communicated through output ports to indicate test results. In this manner, system 10 can be used for as a real-time automated production tester. Other macro applications are possible by recording any sequence of available system functions.

As mentioned previously, system 10 has a great deal of flexibility designed into it which permits it to be built of standard, readily available components. One of the program's features which permit this is the "Configure Video" option available under the "Operations" drop-down menu designated at 124. On activating the "Configure Video" option, the user is presented with other drop-down menus not shown but which the user may elect to introduce "New" information about video camera 24, "Remove" current information, use "Default" information, or "Change" current information. With any of these elections, the user is presented with a subsequent pop-up menu with the dialog boxes and control buttons typically used. With these options, the user fills in the horizontal and vertical percentage modulation of the two-dimensional video sensor of camera 24 as a function of spatial frequency specified in lp/mm. This information is supplied by the manufacturer of the camera selected.

Once the housekeeping functions of selecting and describing the characteristics of the LUT, the type of target to be used (e.g. pinhole, slot, pie segment), and the parameters to be calculated have been completed, a measurement cycle is initiated during which target wheel 50 is quickly rotated under computer control between positions in which a blank is in place across the optical axis to block any IR radiation from passing beyond the blank in the wheel 50 and a position in which a preselected target is placed across the optical path. In the blocking position, a predetermined number of image scans are first stored and then averaged on a pixel-by-pixel basis. The average intensity of each pixel is then calculated to determine the level of background IR radiation, along with any long term drift in the image sensor. Afterwards, the image of the target is scanned and the averages representing the background are subtracted from the intensity values of pixels in the image of the target to arrive at corrected values. The period of time between measurements made with a blocking target and a measurement target is shorter than the time over which there may be an overall change in the background level and/or sensor drift, typically less than one second, which is easily managed via automated switching under software control. This is essential since the temperature of the system may change and thus the background level or sensor noise level.

The algorithm that is used to calculate the line spread function, edge trace and uncorrected and corrected MTF's after determining the background IR level and any image sensor drift is as follows. System 10 is first initialized and configured and the target aligned on the axis of the LUT. This may be done via the various adjustments available in rotary table 20, optical rail 27 and the LUT holder. System 10 is then informed about whether a point or slit target is presented to the LUT. The digitized image from memory 100 is provided, i.e., the intensity at each of the pixels in the image corrected for background IR radiation is known and available as an array. If a point source has been used, the rows and columns of the array of data are summed to generate the two-dimensional or horizontal and vertical line spread functions. The Fourier transform of the horizontal and vertical line spread function is then done to generate the uncorrected MTF. If the corrected MTF is desired, the uncorrected MTF is divided by the MTF or all the other contributing system components. In either case, the result is displayed and also may be outputted to files or other output devices.

The calculations are carried out using the following equations which closely approximate the closed form equivalents:

$$A_c(\theta) = \frac{\sum A(x)\cos 2\pi 0 x \Delta x}{\sum A(x) \Delta x}$$

$$A_c(u) = \frac{\sum A(x)\sin 2\pi u x \Delta x}{\sum A(x) \Delta x}$$

where $\Delta x$ corresponds to pixel separation, $A(x)$ is the value of the line spread function at x obtained by summing columns and normalized to unity at zero spatial frequency, and v is spatial frequency, i.e., $$MTF_{norm} = \frac{MTF(u)}{MTF(0)}$$

The modulation transfer function is then computed by:

$$MTF(u) = \frac{M_i(u)}{M_0(u)}$$

$$M(u) = 1/2 A(v) 1/2 = [A_c^2(v) + A_s^2(v)]^{(1/2)}$$

For a slit target the same equations are used, except that either rows or columns are summed and then the line spread function is integrated and Fourier transformed to obtain the uncorrected MTF with the results displayed corrected or uncorrected as before.

Figure 8:
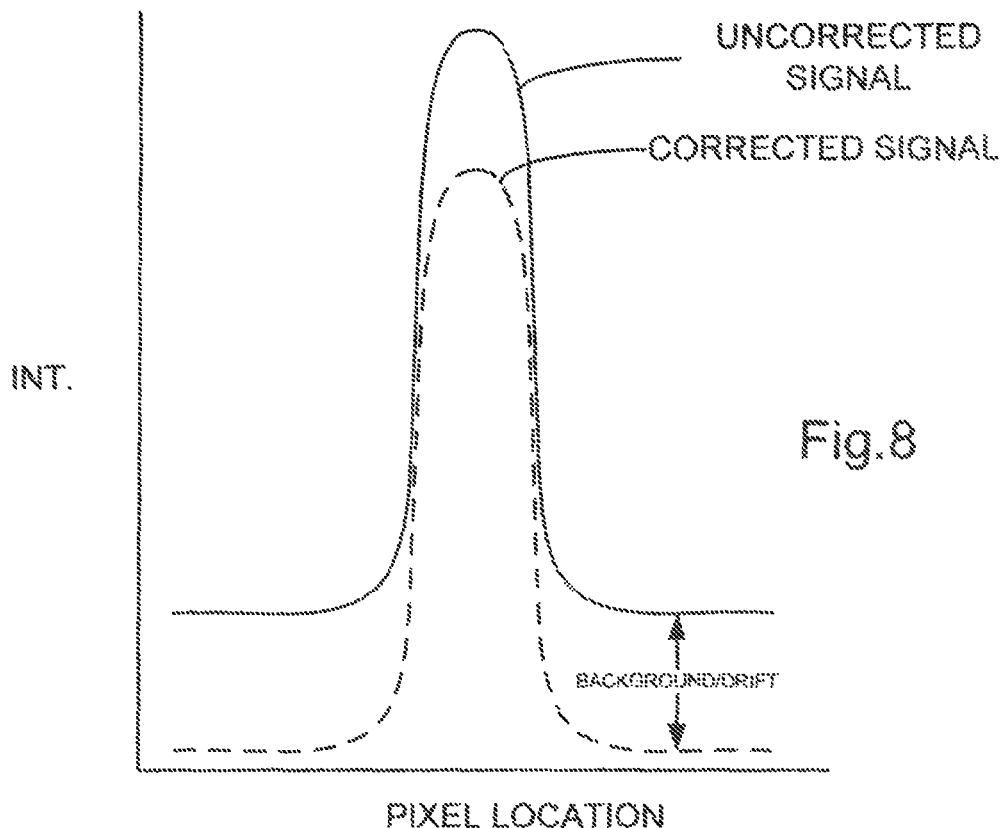
FIG. 8 is a diagrammatic graph comparing intensity measurements of line spread functions compensated and uncompensated for IR background and sensor drift.
Figure 9:
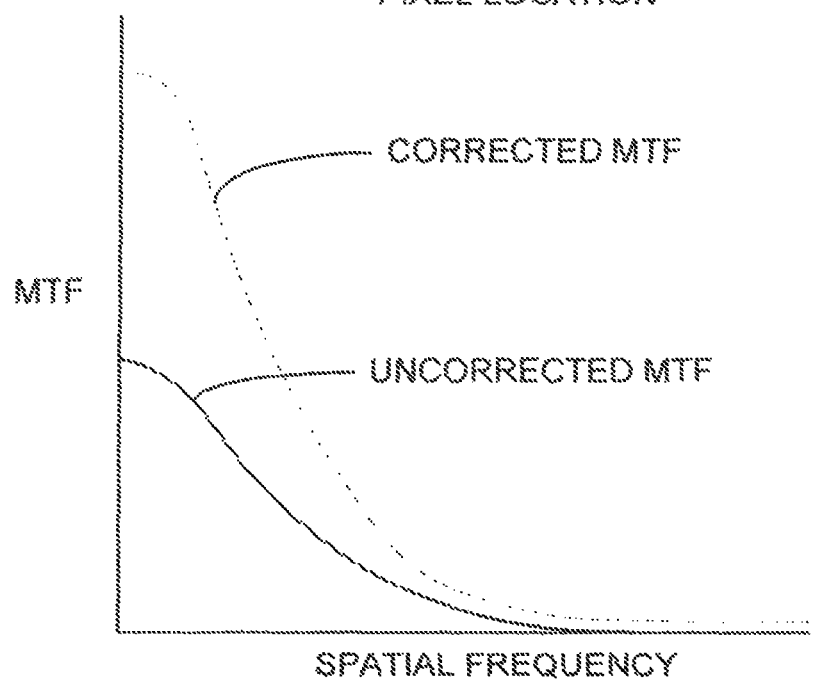
FIG. 9 is a diagrammatic comparison of the MTF curves corresponding to the compensated and uncompensated intensity measurements shown in FIG. 6.

Referring now to FIGS. 8 and 9, there is diagrammatically shown in FIG. 8 a graph depicting the difference between signals corrected for the presence of unwanted IR background radiation in the image data on which MTF and other performance parameters are calculated and signals that have not been corrected. FIG. 9 graphically illustrates the impact that not correcting for IR background radiation and sensor drift has on the determination of MTF. As will be appreciated, small errors in signals can have large impacts on what the MTF of a measured system is believed to be.

A second method for evaluating the level of background IR in the measurement optical path is to incorporate a shutter between the light source and test target. When the shutter is enabled to block the light source from illuminating the test target, the dark frame(s) can be captured. This method has the advantage of higher switching speeds between dark and normal frames suffers from the disadvantage of the slow response times of the light source.

Another method combines one of the above methods with an additional image processing step. One or more dark frames are captured using a blank target or shutter. Then, during normal acquisition, the change in offset from the dark frame is calculated for each frame. Using this method, the DC offset can be recalculated for each frame.

It will also be recognized that analog video IR cameras may be employed to practice the invention. Here, a frame grabber and digitizer are used to convert the analog signal to a digital one using suitable sampling rates. Afterwards, calculations may be carried out in the usual way with the direct digital signal.

Those skilled in the art may make still other changes without departing from the scope of the teachings. Therefore, it is intended that the embodiments shown herein be considered as illustrative and not in a limiting sense.

What is claimed is:

1. Apparatus for testing infrared (IR) optics, said apparatus having an optical path and comprising:
   an arrangement for holding and positioning an IR optic to be evaluated along the optical path so that it can form images when illuminated with IR radiation;
   a source of radiation that emits IR radiation for travel along said optical path over a spectral band that at least encompasses the operating wavelength of the IR optic being tested;
   a mechanism for selectively blocking and unblocking said optical path during a predetermined period, said mechanism having a first position in which it blocks IR radiation and at least one other position in which it presents a preselected transmissive target to said IR optic, the temperature of said mechanism remaining relatively unchanged from the beginning to the end of said predetermined period so that, while blocked, only background IR radiation reaches said IR optic, and while unblocked, IR radiation from said transmissive target, along with background IR radiation, reaches said IR optic;
   an optical system arranged along the optical path for directing IR radiation from said source for travel toward said IR optic, said optical system including a first collimating lens for receiving radiation from said source and generating a collimated beam, a converging lens spaced from said first collimating lens for focusing said collimated beam on said transmissive targets, and a second collimating lens for forming a second collimated beam directed toward said IR optic, wherein said first collimating lens and said second converging lens operate to image said source onto said transmissive targets while imaging the pupil of said first collimating lens over the entrance pupil of said second collimating lens;
   an IR camera having an image detector for observing the image plane of said IR optic to generate images of said blocked optical path and transmissive target the intensity of which said images each vary as a function of spatial location on said IR image detector of said IR camera; and
   a processor for determining from said images the background IR radiation present in said optical path.

2. Apparatus for testing infrared (IR) lens optics, said apparatus having an optical path and comprising:
   an arrangement for holding and positioning an IR lens optic to be evaluated along the optical path so that it can form images when illuminated with IR radiation;
   a source of radiation that emits IR radiation for travel along said optical path over a spectral band that at least encompasses the operating wavelength of the IR lens optic being tested;
   a mechanism located along said optical path for selectively blocking and unblocking said optical path during a predetermined period, said mechanism having one position in which it blocks IR radiation and at least one other position in which it places a preselected transmissive target in said optical path, the temperature of said mechanism remaining relatively unchanged from the beginning to the end of said predetermined period so that, while blocked, only background IR radiation travels to said IR lens optic, and while unblocked, IR radiation from said transmissive target, along with background IR radiation, travels to said IR lens optic;
   an optical system arranged along said optical path for directing IR radiation from said source to illuminate said preselected transmissive target and form an image of said transmissive target for presentation to said IR lens optic, said optical system including a first collimating lens for receiving radiation from said source and generating a collimated beam, a converging lens spaced from said first collimating lens for focusing said collimated beam on said transmissive targets, and a second collimating lens for forming a second collimated beam directed toward said IR lens optic, wherein said first collimating lens and said second converging lens operate to image said source onto said transmissive taraets while imaging the pupil of said first collimating lens over the entrance pupil of said second collimating lens;
   a video IR camera having an two-dimensional IR image detector with a regular array of pixels for observing the image plane of said IR lens optic to acquire images of said blocked optical path and transmissive target where the intensity of said images each vary as a function of their spatial location on said two-dimensional IR image detector of said video IR camera, said two-dimensional IR image detector operating to output digital signals corresponding to each of said image intensities; and
   a processor for receiving said output digital signals and determining therefrom on a pixel-by-pixel basis the background IR radiation present in said optical path.

3. The apparatus of claim 2 wherein said processor further adjusts the intensity levels in the image of said transmissive target to compensate for said background radiation to generate compensated image data representative of the optical properties of said IR optic.

4. The apparatus of claim 3 further including a computer display and wherein said processor further performs image analysis on said compensated image data and displays the results on said computer display as said image analysis is performed.

5. The apparatus of claim 2 wherein said mechanism comprises a rotably mounted target wheel having at least one blank target and at least one transmissive target and is selectively indexable across said optical path between said one blocking position in which said blank target blocks said optical path and said at least one other unblocking position in which predetermined transmissive targets is placed in said optical path.

6. The apparatus of claim 5 wherein said transmissive targets are selected from the group that include pinholes, slits of different width and length, and pie segments.

7. The apparatus of claim 5 wherein said blank target and said transmissive targets are coated with gold to retroreflect unwanted IR radiation that may strike said targets to assure that their temperature is substantially the same during said period.

8. The apparatus of claim 2 wherein said mechanism comprises a shutter positionable across said optical path to selectively block and unblock it and a target wheel rotatably mounted and indexable across said optical path to present different transmissive targets to said IR optic when said shutter is opened to unblock said optical path.

9. The apparatus of claim 2 further including a bandpass filter placed in the collimated beam formed by said first collimating lens to retroreflect IR radiation outside of the operating wavelength of the IR optic back toward said source to prevent unwanted heat from traveling further downstream along said optical path.

10. The apparatus of claim 9 further comprising a source housing for said source, a filter housing connected to said source housing, a housing for said mechanism connected to said filter housing, and a collimating barrel connected to said mechanism housing.

11. The apparatus of claim 10 wherein said source housing includes heat removal elements by which heat built up in said source housing can be dissipated into the surrounding environment.

12. The apparatus of claim 10 wherein said collimated beam formed by said first collimating lens passes through said filter housing and wherein said bandpass filter in positioned in said filter housing in the path of said collimated beam.

13. The apparatus of claim 10 wherein said housings connect to one another with mechanical interfaces that have low heat transmission and thermal masses structured to assure that said mechanism for blocking and unblocking the optical path is uniformly heated.

14. The apparatus of claim 10 wherein said collimating barrel includes internal baffling for preventing ambient IR radiation striking said internal baffling from adding to unwanted IR background radiation.

15. The apparatus of claim 2 wherein said processor is further configured to generate line spread functions for the IR optic and perform Fourier analysis on said line spread functions to generate Modulation Transfer Functions (MTFs) for the IR optic.

16. The apparatus of claim 1 wherein said video IR camera further includes a relay lens having a numerical aperture large enough to capture the light exiting the IR optic under test and being diffraction limited for accurate line spread function and Modulation Transfer Function (MTF) measurements.

17. The apparatus of claim 2 further including a source housing in which said source of radiation resides and at least one other housing connected to said source housing and having said optical system arranged therein along said optical path for directing IR radiation from said source for travel toward said IR optic.

18. The apparatus of claim 17 further including an air gap formed between said source housing and said at least one other housing.

19. The apparatus of claim 1 wherein said IR camera comprises a video IR camera.

20. A method for testing infrared (IR) optics, said method comprising the steps of:
holding and positioning an IR optic to be evaluated along an optical path so that it can form images when illuminated with IR radiation;
directing IR radiation from a source for travel along said optical path toward said IR optic;
selectively blocking and unblocking said optical path over a predetermined period with blank and transmissive targets while maintaining the temperature of said blank and transmissive targets relatively unchanged from the beginning to the end of said predetermined period so that, while blocked, only background IR radiation reaches said IR optic, and while unblocked, IR radiation from said transmissive target along with background IR radiation reaches said IR optic;
coating said blank and transmissive targets with gold so that they retroreflect unwanted IR radiation to assure that they are uniformly heated and maintained at relatively the same temperature during said predetermined period;
observing the image plane of said IR optic with an IR camera to generate images of said blank and transmissive targets the intensity of which vary as a function of spatial location on the IR detector of said IR camera;
determining from the image of the blank target the background IR radiation present in the measurement path;
adjusting the intensity levels in the image of said transmissive target to compensate for said background radiation to generate compensated image data representative of the optical properties of said IR optic; and
performing image analysis on said compensated data and displaying the results as said image analysis is performed.

21. The method of claim 20 further including the step of filtering the IR radiation from the source so that only wanted IR radiation within the operating wavelength range of the IR optic travels to said blank and transmissive targets while unwanted radiation is retroreflected back towards the source.

22. The method of claim 20 wherein said step of performing image analysis further includes determining line spread functions and Fourier analysis to generate Modulation Transfer Functions (MTFs) for the IR optic.

23. The method of claim 20 wherein said transmissive targets are selected from the group including pinholes, slots of differing widths and lengths, and pie shaped segments.

* * * * *